United States Patent [19]

Suto

[11] Patent Number: 5,036,089

[45] Date of Patent: Jul. 30, 1991

[54] 2-OXAZOLIDINONE DERIVATIVES OF NITROIMIDAZOLES AND PHARMACEUTICAL COMPOSITIONS USEFUL AS SENSITIZING AGENTS

[75] Inventor: Mark J. Suto, Ann Arbor, Mich.

[73] Assignee: Warner-Lambert Company, Morris Plains, N.J.

[21] Appl. No.: 534,086

[22] Filed: Jun. 4, 1990

Related U.S. Application Data

[62] Division of Ser. No. 274,209, Nov. 25, 1988, Pat. No. 4,954,515.

[51] Int. Cl.$^5$ ............................................. C07D 263/20
[52] U.S. Cl. ..................................... 514/376; 548/229
[58] Field of Search ......................... 548/229; 514/376

[56] References Cited

U.S. PATENT DOCUMENTS

| | | | |
|---|---|---|---|
| 4,241,060 | 12/1980 | Smithen . | |
| 4,282,232 | 8/1981 | Agrawal . | |
| 4,371,540 | 2/1983 | Lee et al. | 514/398 |
| 4,462,992 | 7/1984 | Agrawal et al. | 514/398 |
| 4,581,368 | 4/1986 | Ahmed et al. | 514/397 |
| 4,596,817 | 6/1986 | Ahmed et al. | 514/397 |
| 4,631,289 | 12/1986 | Ahmed et al. | 514/397 |
| 4,757,148 | 7/1988 | Ahmed et al. | 548/338 |
| 4,797,397 | 1/1989 | Suto et al. | 548/339 |

FOREIGN PATENT DOCUMENTS 0095906 7/1983 European Pat. Off. .

OTHER PUBLICATIONS

J. Med. Chem., 1987, vol. 30, No. 11, p. 2092.
Kano et al., Tetrahedron Letters, pp. 6331–6334, vol. 28, No. 50 (1987).
Evans et al., J. Am. Chem. Soc., pp. 2127–2129, vol. 103 (1981).
Ishizuka and Kunieda, Tetrahedron Letters, pp. 4185–4188, vol. 28, No. 36 (1987).
Kleschick, et al., J. Org. Chem., pp. 3168–3169, vol. 52, No. 14 (1987).
J. Med. Chem., pp. 55–59, vol. 31, No. 1 (1988).
C.A. 102:6544 (1985).
J. Am. Chem. Soc., pp. 6395–6397, vol. 108 (1986).
Tetrahedron Letters, vol. 29, No. 1, pp. 99–102 (1988).

Primary Examiner—Donald G. Daus
Attorney, Agent, or Firm—Joan Thierstein

[57] ABSTRACT

The present invention is novel 2-oxazolidinone analogs of nitroimidazoles; novel pharmaceutical compositions of selected analogs thereof and methods of use for the compositions as radiosensitizing or chemosensitizing agents in the treatment of hypoxic tumor cells.

11 Claims, No Drawings

2-OXAZOLIDINONE DERIVATIVES OF NITROIMIDAZOLES AND PHARMACEUTICAL COMPOSITIONS USEFUL AS SENSITIZING AGENTS

This is a divisional application of U.S. Ser. No. 07/274,209 filed Nov. 25, 1988, now U.S. Pat. No. 4,954,515.

BACKGROUND OF THE INVENTION

The present invention is concerned with a novel, safe, and efficient process for the preparation of known and novel nitroimidazoles and novel intermediates therefor. Also, the invention includes the selected novel nitroimidazoles. The nitroimidazoles both known and novel as well as novel intermediates are sensitizers for radio- or chemotherapy.

Known nitroimidazoles for use as sensitizers are found in U.S. Pat. No. 4,282,232 and various U.S. Pat. Nos. 4,581,368; 4,596,817; 4,631,289; and 4,757,148 claiming British priorities of Serial Nos. 821,5545; and 8231107 (EP equivalent applications No. 83/303063.8) and are all aziridino-containing nitroimidazoles. Disclosed in U.S. Pat. No. 4,596,817 are nitroimidazoles of the general formula

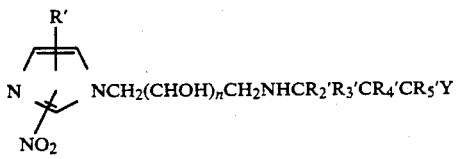

wherein R' is hydrogen or alkyl; n is 1 or 2; R'$_2$–R'$_5$ are hydrogen, alkyl, aryl, aralkyl or alkaryl; and Y is halogen such as bromine or chlorine, shown as intermediates. These also are now found to exhibit activity as sensitizers.

The synthesis of the above-noted references is, for example, generally

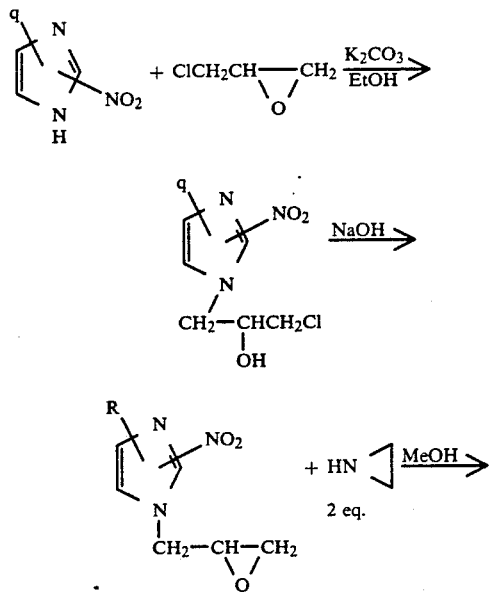

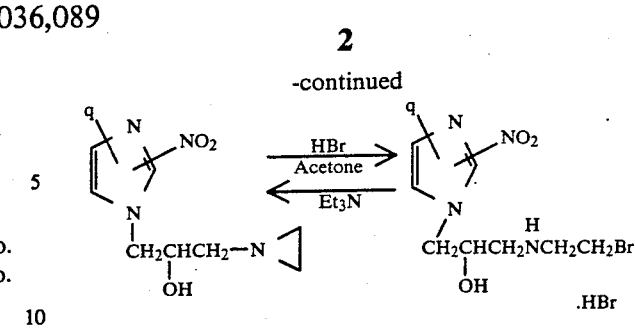

having the disadvantage of poor overall yield. Further, the above synthesis is disadvantageous because it requires the use of the highly toxic, known carcinogenic, ethyleneimine and possibly other highly carcinogenic, ethyleneimine and possibly other highly toxic aziridines. It begins with 2-nitroimidazoles and provides only limited analogous products through a highly unstable aziridine ring containing compound. Particularly, use of ethyleneimine above requires stringent compliance with safety regulations.

On the other hand, the present invention process uses various 2-oxazolidone analogs to provide a wide range of compounds for use as sensitizers having a nitroimidazole ring and is not available to an artisan in prior known references. Thus, the present process shows preparation of both known and novel compounds each having both the nitroimidazole and either 2-oxazolidinone substituents or derivatives of 2-oxazolidinone substituents.

Contrary to the previously known process shown above, the present process provides the desired product in higher yield with fewer process steps and gives products having a predetermined stereochemistry for the substituents noted below as R and R'. That is, in the opening of the aziridine ring in the old methods, a mixture of isomers resulted either which was not separated or for which separations were not readily accomplished, if at all.

Some 2-oxazolidone derivatives and selected processes for making such derivatives are known. For example, the 2-oxazolidone of Musser et al, *J. of Med. Chem.*, p. 2092, Vol. 30, No. 11 (1987) includes a product cyclized from a compound having a phenyl. Kano et al, *Tetrahydron Letters*, pp. 6331-4, Vol. 28, No. 50 (1987); Evans et al, *J. Am. Chem. Soc.*, pp. 2129-31, Vol. 103 (1981); and Ishizuku and Kunieda, *Tetrahedron Letters*, pp. 4185-8, Vol. 28, No. 36 (1987) discloses ring cleavage of an oxazolidone to obtain an amino alcohol. Kleschick et al, *J. Org. Chem.*, pp. 3168-9, Vol. 52, No. 14 (1987) provides cyclization of a side chain attached to the 2-oxazolidone to provide a cyclopropyl containing compound from which the 2-oxazolidone is then removed. However, all of these references fail to teach the steps of the present invention.

Additionally, the presence of both a 2-oxazolidone and an imidazole is shown on an intermediate in the path of metabolism of Metoprolol in *J. Med. Chem.*, pp. 55-9, Vol. 31, No. 1 (1988) and, further, a thiofuran having a cyclized amino alcohol side chain is disclosed as an anticancer agent in C.A. 102:6544 (1985). But again, the present invention is completely different from these disclosures.

Finally, the present invention is also the pharmaceutical compositions and methods of use for the novel nitroimidazoles described herein.

SUMMARY OF THE INVENTION

The present invention as a process for the preparation of a compound of the formula (I″)

$$R_1\text{—}\underset{\underset{\underset{R''}{|}}{\overset{|}{CH_2CH\text{—}(CH_2)_m\text{—}Q''}}}{\underset{N}{\overset{N}{\diagdown}}}\text{—}NO_2 \qquad \text{I''}$$

wherein m, $R_1$, and R″ are as defined below; and Q″ is $$\text{—}\underset{}{N}\overset{\overset{O}{\parallel}}{\diagdown}O, \quad \text{—}\underset{R}{\overset{H}{N}}\text{—}CH\text{—}\underset{R'}{CH}\text{—}X \text{ or } \text{—}N\overset{CHR}{\underset{CHR'}{\diagdown}}$$

wherein X is chloro or bromo; which comprises (1) treating a compound of thhe formula $$\underset{R \quad R'}{\overset{O}{\underset{O}{\diagdown}}\text{—}NR_6} \qquad \text{II}$$

wherein $R_6$ is $$CH_2\text{—}CH\text{—}CH_2 \atop \diagdown O \diagup$$

or $(CH_2)_nCH_2Cl$ wherein n is 1 or 2; with a compound of the formula (III)

$$R_1\text{—}\underset{\underset{H}{|}}{\underset{N}{\overset{N}{\diagdown}}}\text{—}NO_2 \qquad \text{III}$$

wherein $R_1$ is as defined below; in the presence of $K_2CO_3$ or $Cs_2CO_3$ preferably $Cs_2CO_3$ when $R_6$ is $$CH_2CHCH_2 \atop \diagdown O \diagup$$

in a solvent such as an alcohol, preferably ethanol; to obtain a product of the formula (IV)

$$R_1\text{—}\underset{\underset{R_7}{|}}{\underset{CH_2\text{—}CH\text{—}(CH_2)_m\text{—}N}{\overset{N}{\diagdown}}}\text{—}NO_2 \qquad \text{IV}$$

wherein m, $R_1$, R, and R′ are as defined below;

and $R_7$ is hydrogen when $R_6$ is $(CH_2)_nCH_2Cl$ and $R_7$ is OH when $R_6$ is $$CH_2CHCH_2; \atop \diagdown O \diagup$$

and then, alternatively, (2)(a) treating the product of the formula IV with a compound of the formula HX wherein X is as defined above to obtain a product of the formula ($I_1$)

$$R_1\text{—}\underset{\underset{R_7}{|}}{\underset{CH_2\text{—}CH\text{—}(CH_2)_m\text{—}N\text{—}CH\text{—}CH\text{—}X}{\overset{N}{\diagdown}}}\text{—}NO_2 \qquad I_1$$

wherein m, $R_1$ R, R′, $R_7$, and X are as defined below; or (2)(b) treating the product of the formula IV wherein $R_7$ is OH with a compound of the formula $$(R_4CO)_2O$$

wherein $R_4$ is as defined above, in the presence of pyridine and dimethylaminopyridine to obtain the compound of the formula ($I_2$)

$$R_1\text{—}\underset{\underset{OCR_4}{|}}{\underset{CH_2\text{—}CH\text{—}CH_2\text{—}N}{\overset{N}{\diagdown}}}\text{—}NO_2 \qquad I_2$$

and further treating the compound of the formula $I_2$ with a compound of the formula

HX to obtain a compound of the formula ($I_3$)

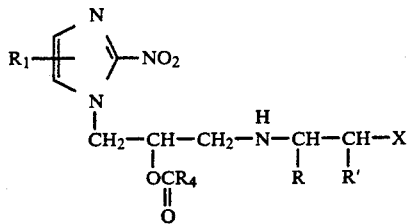

wherein $R_1$, $R$, $R'$, $R_4$, and $X$ are as defined below.

The compound of formula $I_3$ can be treated with triethylamine, preferably 2.1 equivalents in a solvent, such as water or saline, to obtain the compounds of the formula ($I_4$)

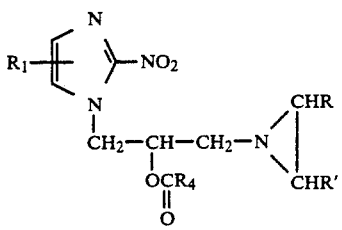

wherein $R_1$, $R$, $R'$, $R_4$ are as defined below.

The invention is also treating, using conditions of known methods or analogous of known methods, a compound of the formula (II'')

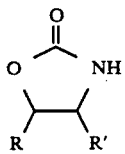

wherein $R$ and $R'$ are as defined below; with a compound of the formula

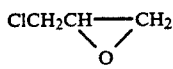

in the presence of sodium in a solvent to obtain a product of the formula (II')

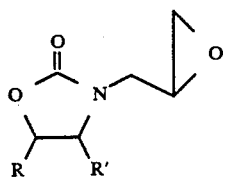

wherein $R$ and $R'$ are as defined below.

The present invention is a compound of the formula (I)

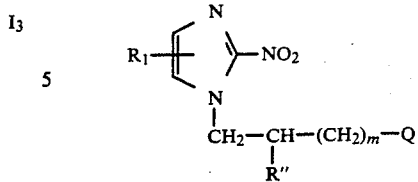

and a pharmacologically acceptable acid addition salt thereof;

wherein m is 0 or 1;

$R_1$ is hydrogen or lower alkyl;

$R''$ is (1) hydrogen or (2) $OR_3$ wherein $R_3$ is H or $$\overset{O}{\underset{\|}{CR_4}}$$

wherein $R_4$ is lower alkyl, aryl, or aralkyl; and Q is

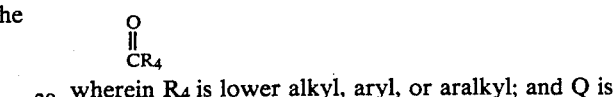

wherein R and R' are independently hydrogen; lower alkyl; aryl; or aralkyl; and X is halogen;

with the proviso that m is 0 or 1 when $R''$ is hydrogen and m is 1 when $R''$ is $OR_3$; and further with the proviso that when $R''$ is OH then Q is not

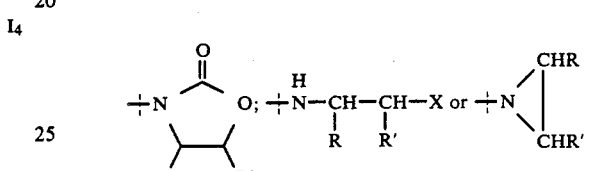

The invention herein is also a method of use for sensitizing hypoxic tumor cells (to the lethal effects of radiation)) comprising administering a compound of the formula (I')

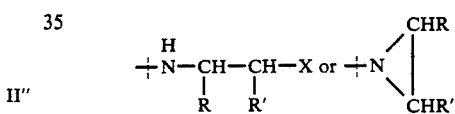

wherein $R_1$ is as defined above; $R_5$ is H or $$\overset{O}{\underset{\|}{OCR_4}}$$

wherein $R_4$ is as defined above and Q' is

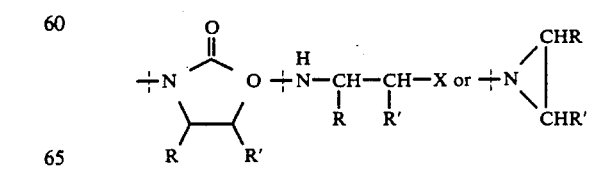

wherein R, R', and X are as defined above; in unit dosage form.

The invention is also a pharmaceutical composition for sensitizing hypoxic tumor cells comprising a sensitizing amount of a compound of the formula I' as defined above together with a pharmaceutically acceptable carrier.

In other words, the novel compounds of the formula I' are useful as radio- or chemosensitizers.

The remaining novel compounds of formula I wherein R" is OH and Q is

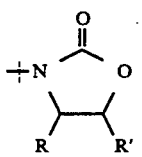

and $R_1$, R, R', X, and m are defined therefor above are useful as intermediates for the process of the present invention to prepare known radiosensitizers and thus also form a part of the present invention.

DETAILED DESCRIPTION OF THE INVENTION

Lower alkyl as used herein is an alkyl group containing one to six carbons. Suitable examples include methyl, ethyl, propyl, butyl, and isomers thereof.

Halogen is chloro or bromo.

Aryl is phenyl unsubstituted or substituted by one or two of lower alkyl, halogen, trifluoromethyl, hydroxy, lower alkoxy, nitro, amino, monoalkyl, or dialkylamino, and the like.

Aralkyl is an aryl attached through an alkylenyl of from one to four straight or branched carbon chains.

The $R_1$ substituent is understood to be in the four or five position of the imidazolyl ring system when numbered as follows:

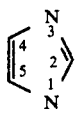

The compounds of the formula I' as defined above are useful in increasing the sensitivity of tumor cells to radiation in radiotherapy and also in potentiating or enhancing damage to tumors by chemotherapeutic agents.

The compound I' may be formulated in a manner appropriate to the treatment for which it is to be used by a composition having the compound I' together with or in association with a pharmaceutically acceptable carrier.

The compound may be included in a dosage form such as a tablet or capsule, for example, a capsule comprising known formulation components such as one or more of those described in Example A of U.S. Pat. No. 4,241,060, which is hereby incorporated by reference. The compound may also be formulated for intravenous administration, e.g., in a saline drip solution.

When employed as a radiation sensitizing agent, in accordance with a further aspect of the present invention, the compound I' is administered to a patient having a radiation sensitive cancer prior to irradiation of said cancer.

The compound I' may, however, in yet a further aspect of the present invention be employed for chemopotentiation of a chemotherapeutic agent by administration of the compound I' to a patient having a localized or metastatic cancer.

Administration of the compound I' is generally carried out prior to or simultaneously with administration of the chemotherapeutic agent, for example, melphalan, cyclophosphamide, or CCNU, i.e. 1-(2-chloroethyl)-3-cyclohexyl-1-nitrosurea.

Activity of the compounds of the formula I' of the present invention is generally shown by the method as shown in, for example, U.S. Patent No. 4,631,289, which is hereby incorporated by reference, particularly in Examples 2 and 3 therein.

The most preferred compound of the present invention is N-(2-bromoethyl)-2-nitro-1-imidazole-1propanamine, or its pharmaceutically acceptable salt.

The following results are shown for the noted examples in which the treatment is intraperitoneally:

| | Radiosensitizing Data | | | | | |
|---|---|---|---|---|---|---|
| Example | SER[1] | Conc (mM) | $C_{1.6}$[2] (mM) | Maximum Tolerated Dose (mg/kg) | Optimum[a] Time (h) | ER[b] (in vivo) |
| 5 | 1.9 | 1.5 | — | — | — | — |
| 8 | 2.6 | 3.0 | 0.44 | 150 | −0.5 | 1.8 |
| 7 | 2.2 | 3.0 | 0.82 | 240 | −1.0 | 1.7 |
| 6 | 1.7 | 0.75 | — | — | — | — |
| 4 | 2.3 | 3.0 | 1.1 | 370 | −0.5 | 1.5 |
| 3 | 1.4 | 1.9 | — | — | — | — |

[1]SER = sensitizer enhancement ratio.
[2]$C_{1.6}$ = concentration which gives an SER of 1.6.
[a]Time of administration prior to irradiation.
[b]Enhancement ratio.

The processes of the present invention are generally accomplished as shown in the schemes:

Scheme A

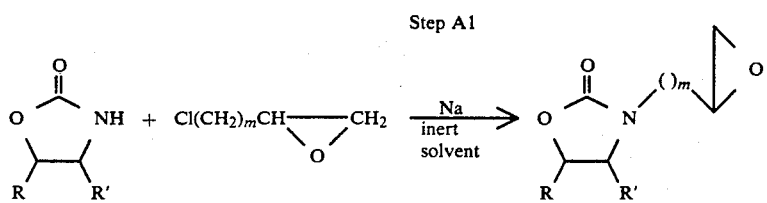

Step A1

II'

Scheme A
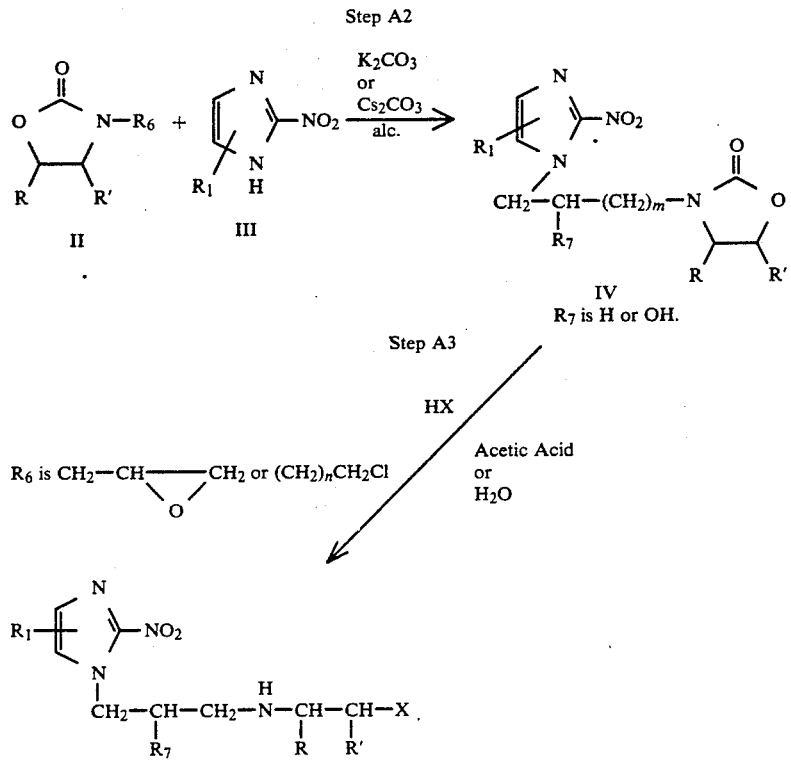
$R_6$ is $CH_2$—CH—$CH_2$ or $(CH_2)_n CH_2Cl$
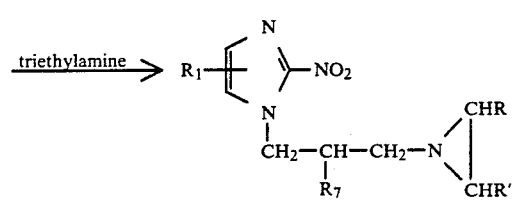
And additionally, the compound of the formula $I_1$ where IV (wherein $R_7$ is OH) can be treated as shown in Scheme B as follows:
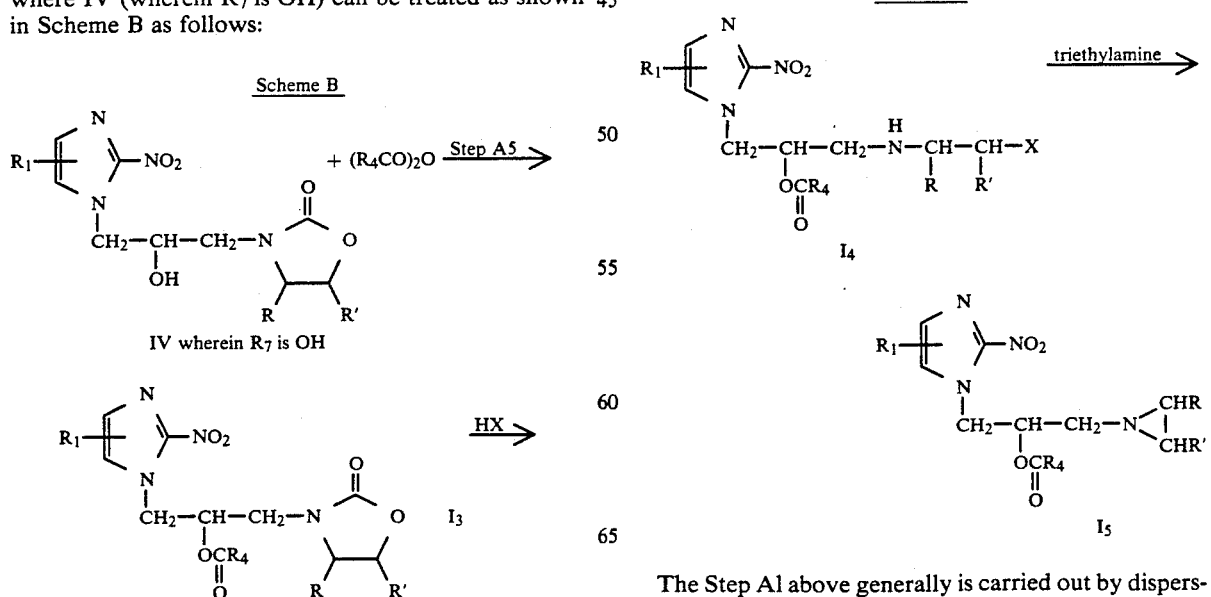
The Step A1 above generally is carried out by dispersing the sodium in an inert solvent such as benzene or toluene, preferably toluene, at reflux temperature. Then the 2-oxazolidone of the formula II is added for from about one to eight hours, preferably four hours, at about room temperature, i.e., 20° -35° C. Then, epichlorohydrin is added at from about -10 to 5° C., preferably 0° C., followed by heating to from 40° to 100° C, preferably 60° C, until TLC provides evidence 0 that the compound of the formula II' is obtained.

The compounds of the formula II" where $R_6$ is $(CH_2)_nCH_2Cl$ are available commercially or can be prepared in a manner as disclosed by R. Dolaby et al in *Ann. Pharm. Franc.* 13, 565 (1955).

Thus, the step A2 generally treats a compound prepared above as II; wherein $R_6$ is

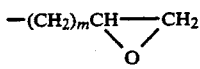

or $(CH_2)nCH_2Cl$, with $K_2CO_3$ or $Cs_2CO_3$ in a protic solvent such as methanol, ethanol, DMF, DMA or the like, preferably DMF, at about 40° to 80° C, preferably 60° C. When $R_6$ is

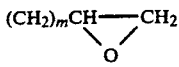

then the preferred reactant is $Cs_2CO_3$ in ethanol. When $R_6$ is $(CH_2)_nCH_2Cl$ then either $K_2CO_3$ or $Cs_2CO_3$ may be preferred.

Finally, Step A3 is generally carried out with the standard commercially available 48% hydrobromic acid as found in the Aldrich catalog or 31% HBr in acetic acid. Equivalent HCl solutions may also be used.

A compound of the formula IV wherein $R_7$ is OH as shown in Scheme B is treated in a solvent, such as pyridine alone or as a mixture with DMF or DMA. The $(R_4CO)_2O$ is added to the compound in the solvent in the presence of catalytic amounts of dimethylaminopyridine (DMAP) and stirred at 20-30° C. until TLC shows the reaction is complete, usually 18-24 hours.

Starting materials required for the processes described in this invention are either commercially available or can be synthesized by methods known in the art.

Variations within the processes of the present invention are understood by one of ordinary skill to be within the invention.

Separation and purification are accomplished by conventional methods.

All examples which follow further illustrate the invention and ar not meant to limit the invention.

PREPARATION 1

3-(Oxiranylmethyl)-2-oxazolidinone Reference: T. Endo et al, *Bull. Chem. Soc. (Japan)* 1969, 42 1101.

A mixture of sodium (12.6 q, 0.6 mol) in 160 ml of toluene was heated to reflux. When the sodium had melted the heat was removed and the mixture was stirred vigorously until it cooled to room temperature. Then 2-oxazolidone (44 g, 0.5 mol) was added and stirring continued for 4.5 hours. The mixture was cooled to 0° C and a solution of epichlorohydrin (78.6 ml, 1.0 mol) in 100 ml of toluene was added dropwise at a rate so the temperature of the reaction was maintained below 5° C. When the addition was complete the mixture was heated at 60° C for 5.5 hours and then at room temperature for 18 hours. The liquid was decanted and concentrated to provide an oil which was distilled to give 24.66 g of the desired compound, 3-(oxiranylmethyl)-2-oxazolidinone (34%); bp 100-120° C., 0.05 mm.

Example 1

2-Oxazolidinone, 3-[2-hydroxy-3-(2-nitro TM 1H]-imidazol-1-yl) propyl]

A mixture of 2-nitroimidazole (8.8 g, 78 mmol) and anhydrous cesium carbonate (0.90 g, 2.8 mmol) was ground to a fine powder and then suspended in 180 ml of anhydrous ethanol. The mixture was heated under reflux for 20 minutes and then 3-(oxiranylmethyl)-2-oxazolidinone from Preparation 1 above (21.1 g, 0.16 mol) was added. The mixture was refluxed for six hours, cooled, and filtered to give 16.3 g (85%) of the desired compound, 2-oxazolidinone, 3-[2-hydroxy-3-(2-nitro-1(2-nitro-1H]-imidazol-1-yl)propyl]; mp 216-218° C.

Example 2

Alpha-(2-bromoethyl)amino]methyl]-2-nitro-1-imidazole-1-ethanol, monohydrobromide To 0.5 g of 2-oxazolidinone, 3-[2-hydroxy-3(2-nitro-1[H]-imidazol-1-yl)propyl](2 mmol) was added 2.5 ml of 31% HBr/acetic acid and the mixture was stirred at room temperature. After 30 minutes all of Example 2 above was dissolved. Stirring was continued for 20 hours, at which time the resulting mixture was diluted with methanol and ether to precipitate the product. The mixture was cooled and filtered to provide 0.78 g of a solid which was recrystallized from methanol to give 0.40 g of the desired product, alpha-[[(2-bromoethyl)amino]methyl]-2-nitro-1-imidazole-1-ethanol, monohydrobromide (54%); mp 159-160° C.

EXAMPLE 3

2-Oxazolidinone, 3-2-(benzoyloxy)-3-(2-nitro-1H-imidazol-1-yl) propyl]

To a mixture of alpha-[[(2-bromoethyl)amino]methyl]-2-nitro-1-imidazoe-1-ethanol, monohydrobromide (2.2 g, 86 mmol), benzoic anhydride (1.98 g, 86 mmol) and dimethylaminopyridine (cat.) was added 36 ml of pyridine. The mixture was stirred at room temperature for 18 hours, concentrated, and partitioned between chloroform and water. The organic layer was dried (MgSO$_4$) and concentrated to a solid which was recrystallized from methanol to give 2.73 g of the desired product, 2-oxazolidinone, 3-[2-(benzoyoxy)-3-(2-nitro-1-imidazol-1-yl) propyl](87%); mp 143-147° C. (dec).

13

Example 4

1H-Imidazol-1-ethanol,[α]-[[(2-bromoethyl)amino]-methyl]-2-nitro-, benzoate, monohydrobromide A mixture of 2-oxazolidinone, 3-[2-(benzoyloxy)-3-(2-nitro-1-imidazol-1-yl) propyl (2.5 g, 69 mmol) in 25 ml of 31% HBr/acetic acid was stirred for 18 hours at room temperature. The solution was diluted with methanol/ether and the resulting precipitate was collected. Recrystallization from methanol gave 2.54 g of the desired product, 1-imidazol-1-ethanol,[α]-[(2-bromoethyl)amino]methyl]-2-nitro-, benzoate, monohydrobromide (77%); mp 170–175° C. (dec).

Example 5

3-[2-(2-Nitro-1H-imidazol-1-yl)ethyl]-2-oxazolidinone

A mixture of 5 g (4 mmol) of 2-nitroimidazole and 6.1 g of $K_2CO_3$ in 50 ml of DMF was heated at 60° C. for 0.5 hours; then 6.61 g (44 mmol) of 3-(2-chloroethyl)-2-oxazolidinone was added and stirring continued for 18 hours; at 60° C. The mixture was then cooled and concentrated. The residue was partitioned between $CHCl_3$ and water, the organic layer was dried and concentrated to a solid. The solid was crystallized from ethanol to give 3.5 g (35%) of the desired product, 3-[2-(2-nitro-1H-imidazol-1-yl)ethyl]-2-oxazolidinone; mp 103–104° C.

EXAMPLE 6

3-[3-(2-Nitro-1H-imidazol-1-yl)propyl]-2-oxazolidinone
A mixture of 6 g of 2-nitroimidazole (53 mmol) and 7.32 g of $K_2CO_3$ was heated at 60° C. for 0.5 hours. Then 8.6 g (53 mmol) of 3-(3-chloropropyl)-2-oxazolidinone (*Ann. Pharm. Franc.*, 13, 565 (1955)) was added and stirring continued for 18 hours at 60° C. The mixture was then cooled and concentrated. The residue was partitioned between $CHCl_3$ and water, the organic layer was dried and concentrated to give 10.4 g of a solid which was recrystallized from ethanol to provide 5.4 g (42%) of the desired product, 3-[3-(2-nitro-1H-imidazol-1-yl)propyl]-1-oxazolidinone; mp 89–91° C.

EXAMPLE 7

N-(2-Bromoethyl)-2-nitro-1H-imidazole-1-ethanamine, monohydrobromide

To 3.5 g (15 mmol) of 3-[2-(2-nitro-1H-imidazol-1-yl) ethyl-2-oxazolidinone was added 30 ml of 31% HBr/acetic acid and the mixture was stirred for 18 hours at 20–25° C. The mixture was diluted with ether and methanol and the resulting solid was collected. Recrystallization from ethanol/water gave 3.0 g of the desired product, N-(2-bromoethyl)-2-nitro-1H-imidazole-1-ethanamine, monohydrobromide (54%); mp 103–104° C.

EXAMPLE 8

N-(2-Bromoethyl)-2-nitro-1H-imidazol-1-promana-mine, monohydrobromide

To 1.0 g (4.16 mmol) of 3-[3-nitro-1H-imidazol-1-yl) propyl-2-oxazolidinone was added 10 ml of 31% HBr/acetic acid and the mixture was stirred for 18 hours at 20–25° C. The mixture was diluted with ether and methanol and the resulting solid was collected. Recrystallization from methanol/$H_2O$ gave 1.22 g of the desired product, N-(2-bromoethyl)-2- nitro-1H-imidazole-1-propanamine, monohydrobromide (80%); mp 164–168° C. (dec).

I claim:

1. A compound of the formula (I)

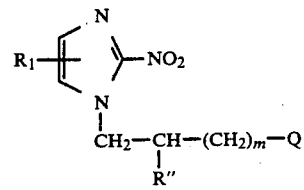

and a pharmacologically acceptable acid addition salt thereof; wherein
m is 0 or 1; $R_1$ is hydrogen or lower alkyl; R" is (1) hydrogen or (2) $OR_3$ wherein $R_3$ is H or

wherein $R_4$ is lower alkyl, aryl wherein aryl is phenyl unsubstituted or substituted by one or two of lower alkyl, halogen, trifluoromethyl, hydroxy, lower alkoxy, nitro, amino, monoalkyl, or dialkylamino, or aralkyl wherein aralkyl is aryl as defined above attached through an alkylenyl of from one to four straight or branched carbon chain; and Q is (1)

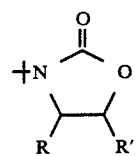

wherein R and R are independently hydrogen; lower alkyl; aryl as defined above, or aralkyl as defined above; with the proviso that m is 0 or 1 when R" is hydrogen; and m is 1 when R" is $OR_3$.

2. A compound of claim 3 wherein m is 0 or 1 and R" is hydrogen.

3. A compound of claim 3 wherein m is 1 and R" is $OR_3$ wherein $R_3$ is

wherein $R_4$ is as defined above.

4. A compound of claim 1 wherein R" is OH and Q is

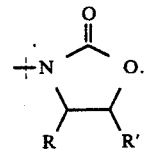

5. A compound of claim 4 which is 3-[2-hydroxy-3-(2-nitro-1[H]-imidazol-1-yl)propyl]-2-oxazolidinone.

6. A compound of claim 3 which is 3-2-(benzoyloxy)-3-(2-nitro-1[H]-imidazol-1-yl)propyl]-2-oxazolidinone.

7. A compound of claim 2 which is 3-[2-(2-nitro-1H-imidazol-1-yl)ethyl]-2-oxazolidinone or 3-[3-(2-nitro-1H-imidazol-1-yl)propyl]-2-oxazolidinone.

8. A pharmaceutical composition for sensitizing hypoxic tumor cells, comprising a sensitizing effective amount of a compound of the formula (I')

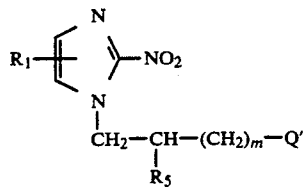

and a pharmacologically acceptable acid addition salt thereof; wherein $R^5$ is H or

wherein $R_4$ is lower alkyl, aryl wherein aryl is phenyl unsubstituted or substituted by one or two of lower alkyl, halogen, trifluoromethyl, hydroxy, lower alkoxy, nitro, amino, monoalkyl, or dialkylamino, or aralkyl wherein aralkyl is aryl as defined above attached through an alkylenyl of from one to four straight or branched carbon chain; $R_1$ is hydrogen or lower alkyl; and Q' is (1)

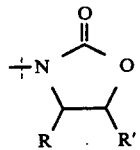

wherein R and R' are independently hydrogen; lower alkyl, aryl as defined above or aralkyl as defined above, wherein m is 0 or 1 when $R^5$ is hydrogen;

and m is 1 when $R^5$ is 

in combination with a pharmaceutically acceptable carrier or diluent.

9. The composition of claim 8 for radiosensitizing hypoxic tumor cells, the amount being a radiation sensitizing amount.

10. The composition of claim 8 for chemosensitizing hypoxic tumoro cells, the amount being a chemotherapeutic sensitizing amount.

11. A method of treating hypoxic tumor cells comprising administering a compound of the formula I' of claim 8 in unit dosage form for sensitizing the cells to radiation or chemotherapy.

* * * * *

UNITED STATES PATENT AND TRADEMARK OFFICE
CERTIFICATE OF CORRECTION

PATENT NO. : 5,036,089

DATED : July 30, 1991

INVENTOR(S) : Mark J. Suto

It is certified that error appears in the above-identified patent and that said Letters Patent is hereby corrected as shown below:

In column 16, line 11, before $$"O\overset{O}{\underset{\|}{C}}R_4"$$

add --and m is 1 when $R^5$ is--.

In column 16, line 15, delete "and m is 1 when $R^5$ is".

In column 14, line 64, change "3-2-(benzoyloxy)-"

to --3-[2-(benzoyloxy)- --.

Signed and Sealed this

Twentieth Day of April, 1993

*Attest:*

MICHAEL K. KIRK

*Attesting Officer*     *Acting Commissioner of Patents and Trademarks*